Figure 1:
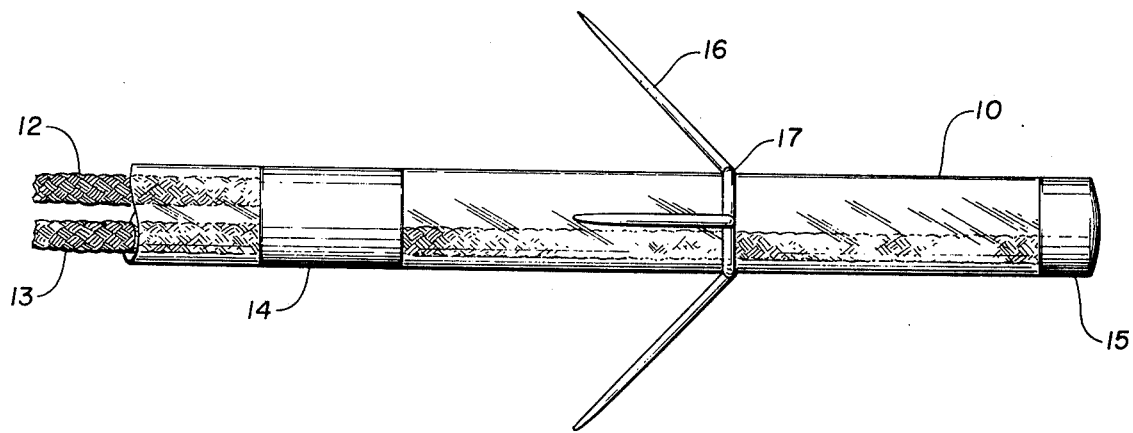

United States Patent [19]

Helland et al.

[11] 4,033,357
[45] July 5, 1977

[54] NON-FIBROSING CARDIAC ELECTRODE

[75] Inventors: John R. Helland; Kenneth B. Stokes, both of Minneapolis, Minn.

[73] Assignee: Medtronic, Inc., Minneapolis, Minn.

[22] Filed: Feb. 17, 1976

[21] Appl. No.: 658,355

Related U.S. Application Data

[63] Continuation-in-part of Ser. No. 547,822, Feb. 7, 1975, abandoned.

[52] U.S. Cl. .......................... 128/418; 128/419 P
[51] Int. Cl.² .................................... A61N 1/04
[58] Field of Search ............ 128/418, 419 P, 404, 128/419 C, 419 E, 348, 350 R; 3/1, 1.1

[56] References Cited

UNITED STATES PATENTS

| | | | |
|---|---|---|---|
| 3,348,548 | 10/1967 | Chardack | 128/418 |
| 3,562,352 | 2/1971 | Nyilas | 3/1 X |
| 3,722,005 | 3/1973 | Cowland | 128/418 X |
| 3,783,868 | 1/1974 | Bokros | 3/1 |
| 3,829,903 | 8/1974 | Stati | 128/348 |
| 3,837,347 | 9/1974 | Tower | 128/419 P X |
| 3,886,947 | 6/1975 | Sawyer | 128/348 |
| 3,902,501 | 9/1975 | Citron et al. | 128/418 |

FOREIGN PATENTS OR APPLICATIONS 1,219,017   1/1971   United Kingdom ............ 128/419 P

OTHER PUBLICATIONS

Kantrowitz et al., "Treatment . . . Implanted Controllable Pacemaker", Surg., Gyn., & Obs., Oct. 1962, pp. 415-420.
Tyers et al., "Nonmetallic . . . Encapsulation", Mat. Inst., vol. 8, No. 2, Mar.-Apr. 1974, pp. 178-179.

*Primary Examiner*—Robert W. Michell
*Assistant Examiner*—Lee S. Cohen
*Attorney, Agent, or Firm*—Schroeder, Siegfried, Ryan & Vidas

[57] ABSTRACT

Non-fibrosing implantable lead apparatus for muscle stimulation, such as cardiac stimulation, comprising an electrode formed from a non-thrombogenic conductive material, a conductor, a conductor encapsulating structure formed from a non-thrombogenic insulating material and a lodging structure for holding said apparatus in a desired position.

11 Claims, 2 Drawing Figures

NON-FIBROSING CARDIAC ELECTRODE

This application is a continuation-in-part of U.S. patent application Ser. No. 547,822 filed Feb. 7, 1975, now abandoned.

In the field of bio-medical devices, various types of implantable stimulators have come into usage. One such stimulator is the cardiac pacer. These devices generally employ one of two types of lead apparatus — epicardial or endocardial — for administering the stimulating pulses to the patient's heart. Epicardial leads have electrodes which are secured directly into the myocardium, through the epicardial surface. Endocardial leads are passed intravenously to the heart and the tip of electrode is lodged in the apex of the right ventricle of the heart.

As the development of improved endocardial leads has progressed, many of the parameters such as physical size, configuration, mechanical and electrical properties have all been considered and their effect upon the safety, long-term reliability and corrosion resistance of the electrodes was thought to have been dealt with sufficiently so that their contribution to electrode performance was thought to be generally understood.

In addition to the above characteristics, a further and not hitherto fully understood characteristic known as the stimulation threshold has also been studied. The stimulation threshold is defined as the minimum level of stimulation (minimum pacing pulse energy) needed to elicit an effective cardiac depolarization, each time the stimulus is applied. The studies of the changes of stimulation threshold of various implanted electrodes over a period of time subsequent to implantation, it has been noted that the stimulation threshold typically increases steadily from an acute threshold at the time of implantation to a relatively high peak value and then decreases from the peak value to a somewhat lower chronic stimulation threshold which, however, is considerably higher than the initial or acute threshold. The complete process which causes this undesirable time varying characteristic of the stimulation threshold of electrodes used for cardiac stimulation has been hypothesized but never fully understood.

It is generally believed that the chronic threshold rise is caused by fibrosis which separates the electrode from stimulatable tissue. Several hypotheses have been advanced to account for the peaking phenomenon and the generation of fibrosis. The cause of fibrosis about the lead has been hypothesized to result from trauma or a "foreign body" reaction. The peaking phenomenon has been hypothesized to be a result of edema or damage to the myocardium. We, however, derived a different hypothesis in our study of the material-blood interface to test our hypothesis tht fibrosis is a response to thrombosis. We were surprised to find that the peaking phenomenon and the chronic threshold rise are partly — but not necessarily only caused by fibrosis about the electrode. The elucidation of the true mechanisms involved in chronic threshold behavior has resulted in the subject invention.

Electrodes which are presently used for cardiac stimulation are manufactured from materials that, although relatively inert, may be termed relatively thrombogenic. That is, the blood's contact with the electrode and lead material initiates a sequence of events that ultimately produces thrombus or blood clot over the portion of the device in contact with the blood. The physiological trauma to cells which occurs due to the incision in the blood vessel when an endocardial electrode is implanted, and at the stimulation site produces tissue thromboplastin — a thrombogenic agent. The presence of thromboplastin in the vicinity of the electrode causes the formation of a thrombus or a fibrin mesh thereon due to the polymerization of fibrinogen in the blood.

It is known that most materials will initiate the clotting mechanism at a blood-material interface. The platinum or platinum alloy conductor and silicone rubber encapsulation or insulation typical of the prior art electrodes, although generally chemically inert to body fluids, will initiate the clotting mechanism and a buildup of a fibrin sheath will occur on the surface initially. Subsequent to the initial buildup, fibrinolysis or dissolving of the clot will occur. Concurrently, collagen will invade the site of the thrombus to stabilize it as has also been known to occur in restricted blood vessels, for example.

The presence of an object such as a lead in the blood flow will cause perturbations in the blood's flow field. If conditions of static or recirculating flow are set up, clotting will occur. In areas of rapid or turbulent flow such as in the heart chambers, the chances for such stagnation are minimal. That this general process is also applicable to cardiac leads is verified by the observation that fibrosis on cardiac leads generally occurs primarily in the vicinity of areas of restricted flow. Typically, for example, fibrosis is observed on the lead in the vicinity of the electrode where it is wedged in the apex and on the silicone rubber insulator where it passes through the cardiac valve. Sections of the lead exposed to regions of high flow, however, are typically free from fibrosis. This observation is noteworthy because silicone rubber compounds which are used to insulate the conductors in prior art leads, although they are generally chemically inert to body fluids, are also known to be thrombogenic to some degree and could, therefore, be expected to produce a thrombus if the other necessary conditions are present.

We have observed that the variations in stimulation threshold during maturation of an implant are consistent with the above processes. First, the stimulation threshold increases as the thrombus or fibrin mesh forms, then stabilizes at a chronic stimulation threshold substantially in excess of the acute or initial stimulation threshold as the collagen stabilizes the sheath. Since both the original fibrin mesh or the resultant collagen plug are non-excitable cardiac tissue, the apparent surface area of the electrode is increased, the current density applied to the excitable tissue is decreased and additional energy is required to apply the stimulation to the excitable cardiac tissue through the layer of non-excitable tissue.

In the prior art, the development of the fibrous layer has generally been believed to be necessary since it serves to prevent the dislodging of the electrode. We have discovered, however, that it is not necessary to rely upon the formation of a fibrous layer over the entire electrode apparatus to maintain electrode position and that it is desirable to substantially reduce the chronic threshold of the cardiac electrode and to minimize or eliminate the peaking of the stimulation threshold which has occurred in the past as the stimulation threshold changes with the time from its acute to its chronic level. The resultant electrode can be operated with a lower power drain on the stimulation pulse generator which thereby either reduces the amount of battery power required and/or increases the operational life of the pacemaker without the necessity of improving the performance of the battery or power source.

We have found — contrary to previous hypotheses — that the development of the fibrous layer or sheath about the lead is dependent upon the materials used in the electrode assembly. Even when fibrosis is eliminated by the use of non-thrombogenic materials in lead construction, mechanical electrode designs which tend to traumatize tissue — such as small diameter spherical or hemispherical designs or designs causing excessive pressure of the electrode on the endocardium caused fibrosis in the myocardium, thus resulting in elevated chronic thresholds. Even when such potentially traumatic electrodes are placed so that no permanent myocardial tissue changes occur — the acute threshold peak was excessively high. We found that it is not only necessary to control fibrosis about the electrode by using non-thrombogenic materials, but to control trauma to the myocardium with blunt electrode designs and to minimize the pressure exerted upon the heart by the lead. Apparently, the effects of physical trauma due to the electrode assembly's physical configuration and the effects caused by the materials used in the electrode assembly are independent contributing factors to the undesired increase in stimulation threshold which has hampered long-term low power operation of prior art stimulation electrodes. Elimination or reduction of only one of the two factors does not provide a proper reduction in the chronic stimulation threshold.

The present invention overcomes the disadvantages of the prior art by elimination of the buildup of a thrombus-like material on a stimulation electrode through the selection of an electrode assembly having a physical configuration lending itself to minimizing trauma to the endocardial tissues at the time of insertion. Fibrous buildup is also minimized through the use of non-thrombogenic materials for both the electrode and the insulating materials used in conjunction with the electrode. Thrombogenic materials are used for the portion of the lead assembly which is used to hold the device in the proper position. Implantable leads made in accordance with our invention have exhibited minimal fibrosis in animal tests and, therefore, have low stimulation thresholds and, accordingly, have reduced the output power demands placed upon the pacemaker for effective stimulation, permitting it to achieve a longer operating life without any change in the capacity of the power sources used.

A primary object of our invention is to provide an implantable stimulation electrode which has a low acute stimulation threshold which does not appreciably increase upon maturation of the implant.

A further object of our invention is to provide an implantable cardiac stimulation electrode assembly which does not cause the growth of a fibrous sheath in the vicinity of the stimulation electrode.

An electrode constructed in accordance with our invention is characterized by a non-thrombogenic conductive electrode in conjunction with a non-thrombogenic encapsulating or insulating material and with means for maintaining the electrode in a desired location.

Figure 2:
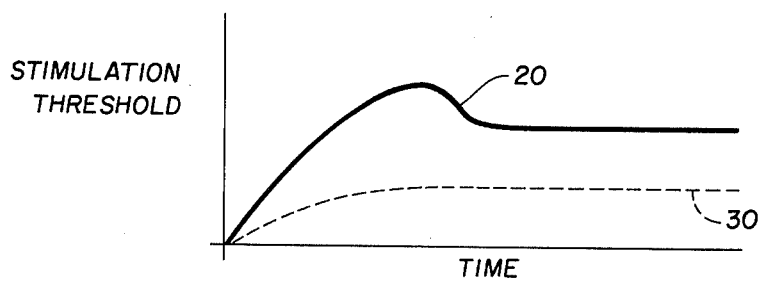

The foregoing and other objects, advantages and characterizing features of an electrode of our invention will become clearly apparent from the ensuing detailed description of the illustrative embodiments thereof, taken together with the accompanying drawings depicting the same wherein:

FIG. 1 illustrates one form of a stimulation electrode according to our invention; and FIG. 2 is a graph illustrating stimulation threshold characteristics as a function of time.

IN THE DRAWINGS

The embodiment shown in FIG. 1 is an electrode configuration of a bipolar endocardial stimulation lead which is normally inserted into the right ventricle of the heart through a vein. The stimulation electrode is formed from a body of an encapsulating or insulating material 10 which encloses a pair of conductors 12 and 13, one preferred form of which being a very pliant multistrand wire of platinum, commonly referred to as "tinsel wire," which are connected in turn to a conductive ring electrode 14 and a conductive tip electrode 15. The free ends of conductors 12 and 13 are connected to a suitable pulse generator (not shown) which applies an appropriate pulse excitation to the conductors.

FIG. 1 also shows a plurality of tines 16 extending at an acute angle from the body member 10 from a position intermediate between the conductive tip electrode 15 and conductive ring electrode 14. The times 16 are of a pliant material which, although it is thrombogenic, is generally inert to body fluids. Silicone rubber is an example of such a material.

The tines may extend from and be unitary with a ring 17 which is adhered to body member 10 in any convenient manner. The tines 16 may take any angle with the body member 10, their purpose being to cooperate with the trabeculae pepillary muscles, and/or other structures of the ventricular endocardium, to maintain the tip 15 in electrical contact with the endocardial tissue.

The construction and use of electrodes similar to the ones shown in FIG. 1, is illustrated, for example, in a patent to W. M. Chardack, 3,348,548, entitled, "Implantable Electrode with Stiffening Stylet." The construction and use of an electrode with tines to hold the electrode assembly in position is shown, for example, in a patent to Paul Citron and Eugene A. Dickhudt, 3,902,501, entitled "Endocardial Electrode."

The material conventionally used for the encapsulation or insulation 10 is a silicone rubber such as the silicone rubber available from Dow Corning Corporation under the trade name Silastic. Although this material is substantially inert and well tolerated by body tissue, it is relatively thrombogenic and fibrotic.

The material most commonly used in the prior art for the conductive ring electrode and the conductive tip electrode is either pure platinum, a platinum alloy such as 90% platinum and 10% iridium, and certain other alloys such as alloys of iron, nickel, cobalt, chromium, and molybdenum under the trade name of Elgiloy, all of which are, as in the case of the silicone rubber insulator, relatively thrombogenic and fibrotic.

In the stimulation electrode of our invention, the buildup of a layer of non-excitable tissue around the electrode is minimized or substantially eliminated by the use of non-thrombogenic materials for both the electrode contacts 14 and 15 and the encapsulating material 10 used to insulate the conductors and to separate the electrodes. Although the buildup of the fibrous sheath normally occurs about the distal end of the lead, including the electrode contacts, we have discovered that the provision of a non-thrombogenic electrode which eliminates this fibrous sheath, does not totally eliminate the problem of increased thresholds. This will occur when the mechanical trauma of the electrode causes the cardic tissue immediately adjacent to the electrode to thicken and become granulated (non-excitable). This results in an increased distance between the electrode and the excitable tissue, thereby increasing thresholds.

In our invention, we have used a non-thrombogenic conductor for the conductive ring electrode 14 and the conductive tip electrode 15. We have found that a very hard pyrolytic carbon coating can be applied to tantalum or other suitable metal electrode to completely cover all exposed surfaces to produce a suitable stimulation electrode having non-thrombogenic characteristics when used in combination with a non-thrombogenic encapsulation material. It is also possible to form the whole electrode from pyrolytic carbon deposited on a graphite substrate. Carbon having suitable pyrolytic properties is manufactured and sold by General Atomic Company of San Diego, Calif., under the trade names LTI Pyrolite Carbon or Hemoplate. A process for making pyrolytic carbon is shown in U.S. Pat. No. 3,399,969 by Jack C. Bokros and Alan S. Schwartz and assigned to Gulf General Atomic Corporation.

We have found that a non-thrombogenic encapsulating or insulating material 10 can be made by applying a polysiloxane-polyurethane block copolymer material of the type manufactured by the Avco Corporation, Cincinnati, Ohio, and sold under the trade name Avcothane, over an extruded polyether urethane tubing. The manufacture of such a coating material is described in a U.S. Pat. No. 3,562,352 by Emery Nyilas entitled, "Polysiloxane-Polyurethane Block Co-Polymers." In addition to having non-thrombogenic properties, the Avcothane coated polyether urethane is a good insulator and has elastomeric properties superior to the silicone rubber normally used for the encapsulating or insulating material. An example of an acceptable extrudable polyether urethane for use in the tubing is Estane 5714F1 manufactured by B. F. Goodrich Co.

Since the use of non-thrombogenic materials for both the electrode and the insulator avoids or minimizes the buildup of fibrous material around the tip of the electrode, it is necessary to provide our stimulation electrode with tines 16 or other lodging means to facilitate lodging of the tip electrode 15 in the trabeculae of the right ventricle of the heart. Lodging means 16 is shown in the preferred embodiment of FIG. 1 located equidistant tip electrode 15 and ring electrode 14.

FIG. 2 illustrates the change in the stimulation threshold, shown along the vertical axis, with time, shown along the horizontal axis. The solid line 20 shows the peaking of the stimulation threshold typical of a conventional electrode in a short time and the eventual decrease in the stimulation threshold to a somewhat lower and substantially constant chronic value. The dashed line 30 shows the gradual increase of the stimulation threshold of an electrode with a non-fibrosing material such as pyrolytic carbon conductive portion and a conventional encapsulating material and having a geometry and construction which minimizes physical trauma. The peaking effect is reduced and the stimulation threshold increases to a chronic value less than that encountered with a conventional lead.

Although the invention has been described with reference to specific preferred embodiment, it is to be understood that the description is solely for the purpose of illustration and that many variations may be made by those skilled in the art without departing from the scope of the invention as set forth in the claims.

It should also be possible to utilize the teachings of the present invention in an epicardial configuration by directly implanting an electrode made of non-thrombogenic materials in the myocardium through the epicardial surface. Since the effects of physical trauma from even an electrode made from non-thrombogenic materials would negate any improvement in chronic stimulation thresholds, it would be necessary to utilize a low trauma myocardial electrode. Conventional myocardial electrodes utilizing a cork screw electrode such as shown in a U.S. Pat. to L. R. Bolduc, No. 3,572,344, "Electrode Apparatus with Novel Lead Construction," do not exhibit any improvement in chronic stimulation threshold by using non-thrombogenic insulator and electrode materials. An electrode formed from non-thrombogenic materials and having a relatively small surface area electrode which has no sharp projections and which is flexible would be expected to have non-thrombogenic characteristics which would achieve stable long-term stimulation threshold characteristics. Also, it is anticipated that the non-fibrotic characteristics of our stimulation electrodes may make them useful for stimulation of non-cardiac muscles and nerves in various applications where it is desirable to have a relatively stable and low stimulation threshold that is not subject to significant degradation upon maturation of the implant of the stimulation electrode and in applications where it is desired that the fibrous buildup on the electrode be minimized to permit relatively easy chronic removal of the stimulation electrode.

Although we have disclosed electrodes which have been formed either from metals over which a non-thrombogenic, hard pyrolytic carbon coating has been applied, or from graphitic carbon substrates upon which pyrolytic carbon has been deposited, it is also possible to form the electrodes entirely from the pyrolytic carbon material.

Although we have shown the use of a non-thrombogenic-polysiloxane polyurethane block copolymer insulating material, it is to be understood that there are other non-thrombogenic insulating materials available. For example, silicone rubber with powdered tungsten incorporated therein is also a non-thrombogenic insulator. This insulating material is shown in U.S. Pat. No. 3,829,903 to Wayne H. Stati and Jack L. Bone entitled, "Method of Inhibiting Blood Clot on Silicone Rubber Medical Devices" and is assigned to Dow Corning Corporation.

In order to provide a redundant protective coating, it has been found useful to coat an electrode made according to our invention in serum albumin or 7% TDMAC (tridodecyl methyl ammonium cholride) Heparin complex manufactured and sold by Polysciences, Inc., Warrington, Pa., to form a non-fibrotic coating over the non-fibrotic electrode.

It is also anticipated that other non-thrombogenic materials may be used for the electrode and insulation without departing from the spirit of our invention some examples of which include electrodes formed from molybdenum, molybdenum/rhodiem alloys and insulators and insulator coatings manufactured from very pure/polyether urethane or polyurea urethane such as those sold by Ethicon Company under the trade name Biomer.

We claim:

1. A non-fibrosing low stimulation threshold lead assembly for permanent implantation in an animal body comprising:
   a. at least one electrode formed from conductive material with at least the body tissue exposed surface thereof formed from a non-thrombogenic material; and
   b. a conductive lead connected to said at least one electrode; and,
   c. encapsulating means with tissue contacting surfaces formed from a non-thrombogenic insulating material, said encapsulating means covering said conductive lead and the connection of said conductive lead to said at least one electrode while leaving a portion of the exposed surface of said at least one electrode exposed for contact with body tissue to be stimulated.

2. A lead assembly as claimed in claim 1 wherein the encapsulating means is formed with a non-traumatic mechanical lodging means to hold the lead assembly in place after it has been implanted in an animal body.

3. A lead assembly as claimed in claim 2 wherein said lodging means is formed from a material being generally inert to body fluids without being non-thrombogenic or non-fibrosing.

4. A lead assembly as claimed in claim 2 wherein said electrode is formed from a non-thrombogenic, hard pyrolytic carbon.

5. A lead assembly as claimed in claim 1 wherein said electrode is formed from a conductive material coated with a non-thrombogenic, hard pyrolytic carbon.

6. A lead assembly as claimed in claim 1 wherein the tissue contacting surface of said encapsulating means is formed from a non-thrombogenic polysiloxane-polyurethane block copolymer.

7. A low stimulation threshold lead assembly for endocardial stimulation usage, comprising:
   a. a generally cylindrical insulator member formed from a non-thrombogenic insulating material;
   b. a smooth, rounded tip electrode attached to a distal end of said cylindrical insulator member, said tip electrode being formed from conductive material with at least the body tissue exposed surface thereof formed from a non-thrombogenic material;
   c. a conductive lead connected to said electrode and enclosed within said insulator member; and,
   d. non-conducting tine means extending from said insulator member and away from said tip electrode from a location displaced from said tip electrode, said tine means forming a generally acute angle with said insulator member and being entirely of a pliant material being sufficiently pliant to prevent penetration of endocardial tissue, said pliant material being generally inert to body fluids without being non-thrombogenic or non-fibrosing.

8. A lead assembly as claimed in claim 7 wherein the tissue contacting surface of said insulator member is formed from a non-thrombogenic polyurea-urethane.

9. A lead assembly as claimed in claim 8 wherein said tip electrode is formed from a conductive material coated with a non-thrombogenic, hard pyrolytic carbon.

10. A lead assembly as claimed in claim 9 including an additional ring electrode made from non-thrombogenic conductive material attached to said generally cylindrical insulator member, a second conductive lead connected to said ring electrode and enclosed within said insulator member, and said non-conducting tine means is attached to said insulator member at a location substantially equidistant between said tip electrode and said ring electrode.

11. A lead assembly as claimed in claim 7 wherein the tissue contacting surface of said insulator member is formed from a polysiloxane-polyurethane block copolymer.

* * * * *

UNITED STATES PATENT AND TRADEMARK OFFICE
CERTIFICATE OF CORRECTION

PATENT NO. : 4,033,357
DATED : July 5, 1977
INVENTOR(S) : John R. Helland; Kenneth B. Stokes It is certified that error appears in the above—identified patent and that said Letters Patent are hereby corrected as shown below:

Column 1, line 55: "tht" should be --that--

Column 4, line 27: "times" should be --tines--

Signed and Sealed this

Twenty-seventh Day of September 1977

[SEAL]

Attest:

RUTH C. MASON
Attesting Officer

LUTRELLE F. PARKER
Acting Commissioner of Patents and Trademarks